United States Patent [19]

James

[11] 4,008,292
[45] Feb. 15, 1977

[54] RECYCLE OF ISOPARAFFIN-BUTYLENE HYDROCARBON TO ISOPARAFFIN-PROPYLENE ALKYLATION REACTION

[75] Inventor: John P. James, Sweeny, Tex.

[73] Assignee: Phillips Petroleum Company, Bartlesville, Okla.

[22] Filed: Feb. 13, 1976

[21] Appl. No.: 657,817

[52] U.S. Cl. .......................................... 260/683.45
[51] Int. Cl.[2] ........................................... C07C 3/54
[58] Field of Search ................. 260/683.45, 683.48

[56] References Cited

UNITED STATES PATENTS

| | | | |
|---|---|---|---|
| 2,312,539 | 3/1943 | Frey | 260/683.45 |
| 3,080,438 | 3/1963 | Sailors | 260/683.48 |
| 3,113,987 | 12/1963 | Hutson, Jr. | 260/683.45 |
| 3,787,518 | 1/1974 | Anderson | 260/683.45 |
| 3,867,473 | 2/1975 | Anderson | 260/683.45 |
| R28,724 | 2/1976 | Sobel | 260/683.45 |

Primary Examiner—George Crasanakis

[57] ABSTRACT

An alkylation process and apparatus are disclosed wherein a butylene alkylation and a separate propylene alkylation are carried out and in which a portion of the hydrocarbon effluent from the butylene, alkylation zone is introduced into the propylene alkylation zone.

8 Claims, 1 Drawing Figure

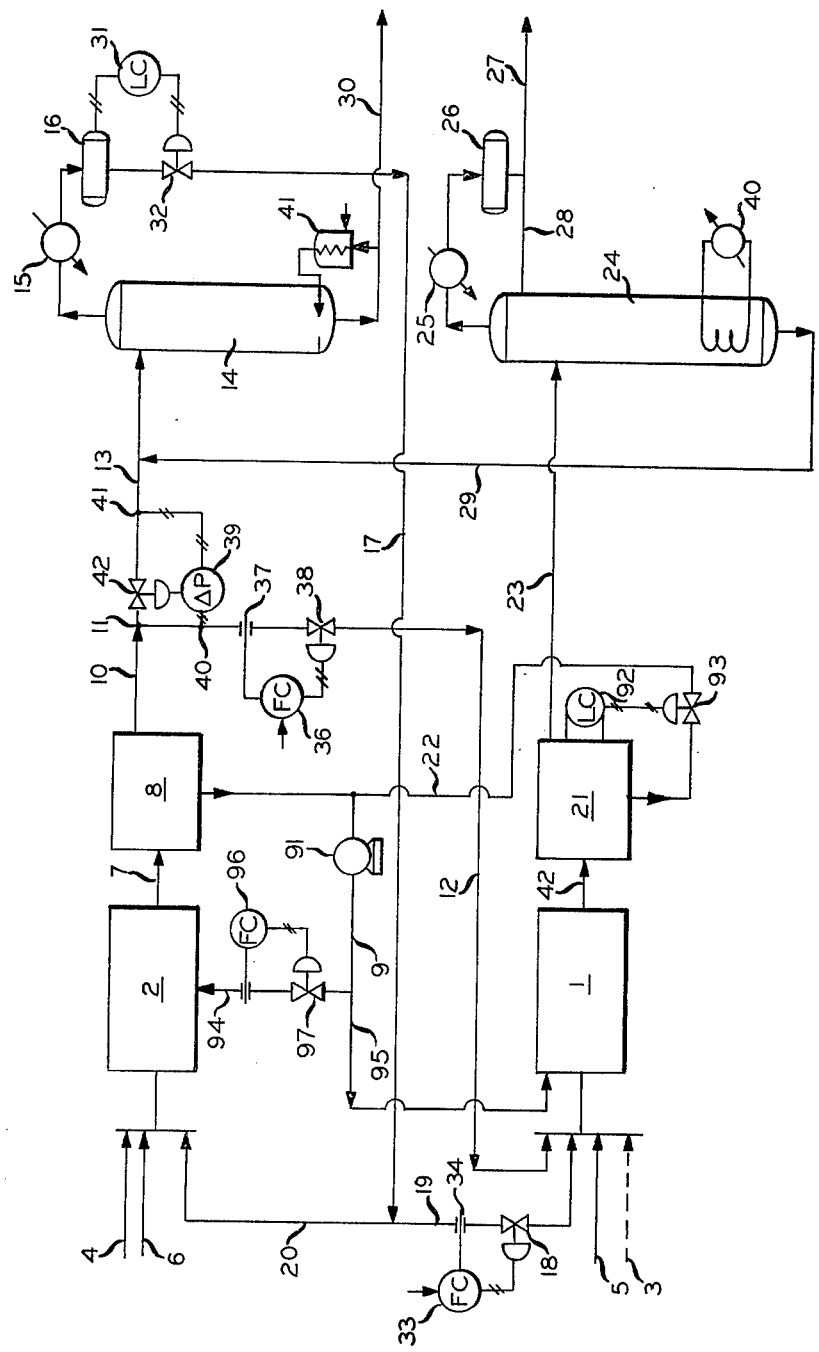

RECYCLE OF ISOPARAFFIN-BUTYLENE HYDROCARBON TO ISOPARAFFIN-PROPYLENE ALKYLATION REACTION

The present invention relates to HF alkylation. In accordance with one aspect, the present invention relates to an HF alkylation process with two separate alkylation zones.

BACKGROUND OF THE INVENTION

It is known in the art that isoparaffins and monoolefins can be reacted in the presence of an HF catalyst to produce higher molecular weight hydrocarbons. This alkylation process has found widespread use for the production of high octane gasoline. It is further known in the art that isoparaffins can be alkylated optimumly, separately by butylenes and by propylenes. It has also been proposed in the art to recycle the unreacted isoparaffin which is separated from the alkylate in an isoparaffin stripper. It is further known in the art that a portion of the effluent of a first alkylation reactor can be either recycled directly to this reactor or to another HF alkylation reactor in which the same alkylation reaction is carried out as in the first alkylation reactor. In the latter case, the two reactors in which the same alkylation reaction occurs are quasi connected in series.

The introduction or recycling of hydrocarbon effluent into the alkylation zone is reported to improve the octane number of the alkylate produced. Recycling total reactor hydrocarbon effluent from a HF butylene/isoparaffin alkylation reactor has the advantage of increasing the isoparaffin butylene ratio without increasing the load on the isostripper. However, this procedure has the disadvantage over recycling pure isoparaffin of increasing the production of heavy hydrocarbons such as fractions with 12 carbon atoms or more per molecule. It would thus be desirable to have an alkylation process available that can be operated at high isoparaffin/olefin rate, and at the same time produces only a minimum amount of heavy hydrocarbons and does at the same time not increase the utilities required, particularly for the isoparaffin stripper.

THE INVENTION

It is thus one object of this invention to provide a new alkylation process.

Another object of this invention is to provide an alkylation process using high ratio of isoparaffin to olefin in the reactor without increasing the load on the isoparaffin stripper, and with only a limited amount of production of heavy hydrocarbons.

Still a further object of this invention is to increase the isoparaffin to alkylate ratio of an HF alkylation process.

These and other objects, embodiments, advantages, details and features of this invention will become apparent to those skilled in the art from the following detailed description of the invention, the examples, the appended claims and the drawing which shows a schematic flow diagram for the process of this invention.

In accordance with this invention, there is now provided an alkylation process in which a portion of the hydrocarbon effluent of a butylene-isoparaffin-alkylation zone is introduced into a propylene-isoparaffin-alkylation zone. By this process two essential advantages are achieved. The introduction of hydrocarbon reactor effluent from the butylene-isoparaffin-alkylation zone is made into a less sensitive system. Thus although as desired the isoparaffin to olefin ratio in the propylene-isoparaffin-alkylation zone is thereby increased, the production of heavy hydrocarbons is decreased and the heavy hydrocarbons that are produced generally have a lower number of cabon atoms per molecule than would be the case if the portion of the reactor effluent would be introduced into a butylene-isoparaffin-alkylation zone, such as the butylene-isoparaffin-alkylation zone from which this effluent originated.

In the HF alkylation process described, the isoparaffin to butylene mol ratio generally is at least 10 to 1. The isoparaffin to propylene mol ratio in the propylene-isoparaffin-alkylation zone is at least about 10 to about 1. The volume ratio of catalyst to hydrocarbon broadly speaking is from 1:10 to 8:1, depending particularly on the cooling system. In those systems where the reactor is indirectly cooled, the catalyst/hydrocabon volume ratio is in the range from 1:1 to 1:10. If the catalyst stream is cooled, the catalyst/hydrocarbon volume ratio is in the range from 2:1 to 8:1.

The portion of the hydrocarbon effluent from the butylene-isoparaffin-alkylation zone, which is introduced into the propylene-isoparaffin-alkylation zone is not critical except that the portion is designed such that the desired isoparaffin to propylene ratio is achieved and propane is removed from the butylene system. As a general rule, the portion of the butylene-isoparaffin-alkylation zone introduced into the propylene-isoparaffin-alkylation zone will be in the range of 30 to 60 volume percent of the total hydrocarbon effluent from the butylene-isoparaffin-alkylation zone.

A high isoparaffin to butylene ratio in the butylene alkylation zone is achieved in accordance with a preferred embodiment of this invention by recycling the isoparaffin removed from that portion of the hydrocarbon effluent from the butylene-isoparaffin-alkylation zone that has not been introduced into the propylene-isoparaffin-alkylation zone, as well as the isoparaffin removed from the hydrocarbon effluent from the propylene-isoparaffin-aklylation zone. Thereby, only isoparaffin and no alkylate is reintroduced into the butylene alkylation zone so that only a minimal amount of heavy hydrocarbons is formed while at the same time the isoparaffin to butylene ratio is considerably increased.

In accordance with another embodiment of this invention, the hydrocarbon effluent from the propylene-isoparaffin-alkylation zone is passed to a depropanizing column, the bottoms from the depropanizing column are introduced to an isoparaffin stripping column and the portion of hydrocarbon effluent from the butylene-isoparaffin-alkylation zone, which has not been introduced into said propylene-isoparaffin-alkylation zone, is also passed into the same isoparaffin stripping column. The depropanizing column and the isoparaffin stripping column can be portions of one column. The isoparaffin leaving the isoparaffin stripping zone overhead is introduced into the butylene-isoparaffin-alkylation zone, whereas the alkylate bottom from the isoparaffin stripping zone comprising a blend of alkylates from zones 1 and 2 is recovered as the product of the process.

Feed streams utilized in this process are feed streams which as such are generally used in the HF alkylation art. The isoparaffin generally is composed of isobutane and isopentane. The alkylating agent for the butyleneisoparaffin-alkylation zone consists primarily of butylenes, particularly of isobutylene and some n-butylenes. The alkylating agent for the propylene-isoparaffin-alkylation zone consists predominantly of propylene. The HF catalyst used in the process both in the butylene-isoparaffin-alkylation zone and in the propylene-isoparaffin-alkylation zone is hydrogen fluoride, usually having water in a quantity of up to about 5% by weight of the catalyst.

The reactor effluent from both alkylation zones is passed to separate settlers in which the hydrocarbon phase and the catalyst or HF phase separate. The catalyst phase is either recycled into the respective alkylation zone, or the two catalyst phases from the two settlers are mixed and passed through one pump and the resulting catalyst stream is split up to be reintroduced into the two alkylation reactors, whereas the hydrocarbon phase is further processed as described above.

Further details and preferred embodiments will become apparent from the following description of the drawing, as well as the calculated example.

In the drawing a first propylene-isoparaffin-alkylation zone 1 is provided for. Correspondingly, a second butylene-isoparaffin-alkylation zone 2 is used for alkylating the isoparaffin by butylene. Fresh or reactant isoparaffin is introduced into the butylene alkylation zone 2 by way of line 4. Propylene as the alkylating agent to the first alkylation zone 1 is introduced via line 5. Butylenes are the alkylating agent for the second alkylation reactor 2. These are introduced into this reactor via line 6.

The effluent from the second butylene-isoparaffin-alkylation zone is passed via line 7 to a separator 8. From this separator 8 the catalyst phase is recylcled via pump 91 and lines 9 and 94 into the butylene-isoparaffin-alkylation zone 2. The hydrocarbon effluent is withdrawn from the separator 8 via line 10 and is split at the point 11 into a first and a second portion. The first portion is passed via line 12 into the propylene-isoparaffin-alkylation zone 1. The second portion of the hydrocarbon reactor effluent is passed via line 13 onto the top tray of the main fractionation tower or isoparaffin stripping zone 14, which is equipped with a reboiler 41.

The overhead from the isoparafin stripping zone 14 is passed through a condenser 15 and an accumulator 16. The accumulated overhead consisting essentially of isoparaffin is passed via line 17 to be recycled in part via line 20 into the butylene-isoparaffin-alkylation zone 2. A valve 18 in a line 19 is provided for connecting the recycle line 17 to the first propylene-isoparaffin-alkylation zone. By way of this line 19, isoparaffin is charged at a constant preselected flow rate into the propylene alkylation zone 1.

The effluent from the propylene-isoparaffin-alkylation zone 1 is passed via line 42 to a settler 21. From this settler the HF or catalyst phase is withdrawn via line 22 by the pump 91. The quantity of catalyst withdrawn is controlled by level controller 92 and valve 93. The catalyst stream in line 9 is split into a first stream in line 95 that is introduced into the propylene-isoparaffin-alkylation zone 1 and into a second stream in line 94 that is introduced into the butylene-isoparaffin-alkylation zone 2. The flow in line 94 is kept contant by flow controller 96 and valve 97. Separate recycle loops for the catalyst are also possible. The hydrocarbon effluent from the settler 21 is passed via line 23 to a depropanizer 24, which is equipped with a reboiler 40. The overhead effluent from this depropanizer 24 is passed via a condenser 25 and an accumulator 26 to line 27 from which the propane is recovered. A portion of the accumulated overhead, consisting essentially of propane, is reintroduced into the depropanizer 24 as a reflux via line 28. The bottom leaving the depropanizer 24 is passed via line 29 into the isoparaffin stripping zone 14.

The bottom effluent leaving the isoparaffin stripping zone 14 consists essentially of normal butane and alkylate and is recovered via line 30. A vapor sidedraw of normal butane can be removed from a lower portion of tower 14 or stream 30 can be charged to a debutanizer.

A level controller 31 is attached to the accumulator 16. This level controller 31 actuates a valve 32 and thus controls the flow of the recycled hydrocarbon. The quantity of isoparaffin from the isoparaffin stripping zone, which is introduced into the propylene reactor, is controlled by a flow controller 33 which senses the flow of isoparaffin at 34 and correspondingly actuates a valve 18. The flow thru valve 18 is controlled by flow controller 33 at a preselected value.

Another flow controller 36 controls the quantity of hydrocarbon effluent from the butylene-isoparaffin-alkylation zone into the propylene-isoparaffin-alkylation zone. This flow controller 36 senses the flow of hydrocarbon effluent in line 12 at 37 and correspondingly actuates a valve 38.

A pressure controller 39 is provided for which senses the pressure differential between the lines 12 and 13 at the locations 40 and 41 respectively. The pressure controller 39, responsive to the pressure differential sensed, actuates valve 42.

The invention will still be more fully understood from the following calculated example.

EXAMPLE

This example shows material balance calculation comparing two modes of operation. The operation in accordance with this invention and the results that can be obtained are shown in the right column, whereas the left column of the material balance calculation shows the flow rates and ratios and other values for the case in which no hydrocarbon effluent from the butylene-isoparaffin-alkvlation zone 2 is introduced into the propylene-isoparaffin-alkylation zone 1. The results in the left column in other words describe an operation without line 12 or with the valve 38 closed, and with the stoichiometric amount of fresh isobutane being injected either totally into the isostripper overhead accumulator, vessel 16, or metered individually via lines 3 and 4 into each separate propylene- or butylene-isoparaffin-alkylation reaction zone. The values shown in the following table are barrels per hour unless otherwise indicated.

TABULATION

| Unit 2 | | System Without Line (12) | Invention |
|---|---|---|---|
| (6) | Olefins | 146 | 146 |
| | Butylenes, 42 vol % | | |
| | Propylene, 9 vol % | | |
| | Amylenes, 1 vol % | | |
| | Total Flow in (6) | 280 | 280 |
| (4) | Isobutane Feed (98.5% Pure) | 91 | 240 |
| (20) | Recycle Isobutane (88% Pure) | 1430 | 2308 |
| | Isobutane | 1258 | 2031 |
| Unit 2 Isobutane/Olefin Vol. Ratio | | 9 | 16 |
| Unit 2 Hydrocarbon/Catalyst Vol. Ratio | | 9.4 | 9.4 |
| (10) | Hydrocarbon Effluent | 1755 | 2785 |
| (12) | Hydrocarbon to Unit 1 | 0 | 1514 |
| (13) | Hydrocarbon to Isostripper | 1755 | 1271 |
| (29) | Hydrocarbon from Depropanizer to Isostripper | 1262 | 1771 |
| (30) | Total Alkylate Stream | 474 | 499 |
| | Debutanized Alkylate | 440 | 465 |
| | (a) Gasoline Alkylate | 414 | 439 |
| | Research Octane No. Clear on (a) | 90.8 | 91.8 |
| (17) | Recycle Isobutane (88% Pure) | 2543 | 2543 |
| (19) | Recycle Isobutane (88% Pure) | 1113 | 235 |
| (3) | Isobutane Feed (98.5% Pure) | 107 | 0 |
| (5) | Olefins | 101 | 101 |
| | Propylene, 62 vol % | | |
| | Butylenes, 10 vol % | | |
| | Total Flow in (5) | 150 | 150 |
| Unit 1 Isobutane/Olefin Vol. Ratio | | 11 | 14 |
| Unit 1 Hydrocarbon/Catalyst Vol. Ratio | | 9.4 | 9.4 |
| (23) | Feed to Depropanizer | 1310 | 1813 |
| (27) | Propane Yield | 48 | 42 |

The temperature used in the butylene-isoparaffin-alkylation zone is about 90°F and that in the propylene-isoparaffin-alkylation zone can be about 90°F to about 120°F. These temperatures are typical not not limiting in any way. It is more desirable to operate the butylene-isoparaffin-alkylation reactor at a lower temperature than the propylene-isoparaffin-alkylation reactor. The pressures used in both alkylations are sufficient to maintain liquid phases.

The above figures show both increased isoparaffin to olefin ratios and an increased octane of alkylate and slightly more production. The results also show that this is achieved without significantly increasing the load of the isostripper 14.

Reasonable variations and modifications, which will be apparent to those skilled in the art can be made in this invention without departing from the spirit and scope thereof.

I claim:

1. An alkylation process in which an alkylate is produced from an isoparaffin having 4 to 6 carbon atoms and a monoolefin having 3 to 5 carbon atoms comprising
   a. contacting a first isoparaffin feed stream with a propylene stream and a hydrogen fluoride alkylation catalyst in a first alkylation zone,
   b. removing a first alkylation effluent from said first alkylation zone and separating it into a first catalyst phase and a first hydrocarbon phase,
   c. contacting a second isoparaffin feed stream with a butylene stream and a hydrogen fluoride alkylation catalyst in a second alkylation zone,
   d. removing second alkylation effluent from said second alkylation zone and separating it into a second catalyst phase and second hydrocarbon phase,
   e. splitting said second hydrocarbon phase into a first portion and a second portion,
   f. introducing said first portion of said second hydrocarbon phase into said first alkylation zone,
   g. recovering the alkylation product from the second portion of said second hydrocarbon phase and from said first hydrocarbon phase.

2. A process in accordance with claim 1 wherein said second portion of said second hydrocarbon phase is passed to an isoparaffin stripping column, wherein isoparaffin is removed overhead from said isoparaffin stripping column and wherein alkylate is removed from said isoparaffin stripping column as a bottom effluent.

3. A process in accordance with claim 1 wherein said first hydrocarbon phase is passed to a depropanizing column, wherein propane is removed overhead from said depropanizing column and wherein undebutanized alkylate and isoparaffin are removed from the bottom of the depropanizing columm.

4. A process in accordance with claim 2 wherein said isoparaffin which is removed from said isoparaffin stripping column is reintroduced into said second alkylation zone.

5. A process in accordance with claim 1 wherein the catalyst phases are reintroduced into the alkylation zones.

6. A process in accordance with claim 2 wherein said first hydrocarbon phase is introduced into a depropanizing column, wherein propane is removed overhead from said depropanizing column, wherein the bottom effluent from said depropanizing column is introduced into said isoparaffin stripping column and wherein the isoparaffin removed from said isoparaffin stripping column is introduced into said second alkylation zone.

7. A process in accordance with claim 1 wherein said first portion of said second hydrocarbon phase is about 30 to about 60 vol % of said second hydrocarbon phase.

8. A process in accordance with claim 1 wherein all the stoichiometrically required isoparaffin fresh feed for both the propylene alkylation in the first alkylation zone and the butylene alkylation in the second alkylation zone is introduced into the second alkylation zone.

* * * * *